(12) United States Patent
Tamada et al.

(10) Patent No.: US 6,559,937 B2
(45) Date of Patent: May 6, 2003

(54) INSPECTION APPARATUS AND METHOD

(75) Inventors: Hitoshi Tamada, Kanagawa (JP); Yutaka Imai, Tokyo (JP); Ayumu Taguchi, Tokyo (JP); Hiroyuki Wada, Kanagawa (JP)

(73) Assignee: Sony Corporation, Tokyo (JP)

( * ) Notice: Subject to any disclaimer, the term of this patent is extended or adjusted under 35 U.S.C. 154(b) by 111 days.

(21) Appl. No.: 09/727,143

(22) Filed: Nov. 30, 2000

(65) Prior Publication Data

US 2001/0021014 A1 Sep. 13, 2001

(30) Foreign Application Priority Data

Dec. 3, 1999 (JP) ............................................. 11-345465

(51) Int. Cl.[7] .............................................. G01N 21/00
(52) U.S. Cl. .................................................. 356/237.2
(58) Field of Search ........................... 356/237.1, 237.2, 356/237.4, 237.5

(56) References Cited

U.S. PATENT DOCUMENTS

| | | | |
|---|---|---|---|
| 4,598,998 A | * | 7/1986 | Kamei et al. ............. 356/237.5 |
| 4,641,967 A | | 2/1987 | Pecen |
| 4,724,322 A | | 2/1988 | Knowles et al. |
| 4,952,058 A | | 8/1990 | Noguchi et al. |
| 5,151,584 A | | 9/1992 | Ebbing et al. |
| 5,486,919 A | * | 1/1996 | Tsuji et al. ............... 356/237.4 |
| 6,400,454 B1 | * | 6/2002 | Noguchi et al. ......... 356/237.3 |

* cited by examiner

Primary Examiner—Michael P. Stafira
(74) Attorney, Agent, or Firm—Sonnenschein, Nath & Rosenthal

(57) ABSTRACT

An image of an inspection target having a concave and convex pattern is picked up in an off-focus state by an image pickup element 4. Further, the image of the inspection target picked up in the off-focus state is taken in by an image processing computer 6. Based on the image, the image processing computer 6 prepares a light intensity profile having a peak corresponding to a boundary portion between a concave portion and a convex portion of the concave and convex pattern of the inspection target. For example, a change of the width of the concave or convex portion of the concave and convex portion can be detected very accurately, by measuring the width of the concave or convex portion of the concave and convex portion on the basis of the intensity profile.

13 Claims, 6 Drawing Sheets

INSPECTION APPARATUS AND METHOD

RELATED APPLICATION DATA

The present application claims priority to, Japanese Application No. P11-345465 filed Dec. 3, 1999, which application is incorporated herein by reference to the extent permitted by law.

BACKGROUND OF THE INVENTION

The present invention relates to an inspection apparatus used for inspecting a device such as a semiconductor integrated circuit or the like which has a micro concave and convex pattern, and an inspection method for inspecting a micro concave and convex pattern.

In recent years, the integration rate of semiconductor integrated circuit has been improved as digitalization has been developed in the electric industrial field. How this highly integrated semiconductor circuit can be efficiently supplied at low costs is a significant problem that will decide future progress in the digital electronic industrial field.

To produce efficiently semiconductor integrated circuits at low costs, it is important to find rapidly a problem which occurs during the manufacturing process, such as a change or the like of a line width of a micro pattern, to find the cause of the problem, and to make an effective countermeasure for the manufacturing equipments or manufacturing process. Therefore, there is a greater demand for an inspection apparatus capable of inspecting a micro pattern.

Known as inspection apparatuses having a high resolution are those using a scanning electron microscope (SEM), an atomic force microscope (AFM), and the like. However, these scanning electron microscopes and atomic force microscopes require vacuum in inspection, and are therefore inconvenient for handling. In addition, it takes much time to inspection entirely a semiconductor device.

In contrast, an inspection apparatus using an optical microscope is advantageous in that inspection can be carried out undestructively without necessitating vacuum or contact. However, the patterns of semiconductor integrated circuits have become more and more micro in recent years, so that the line width have been decreased to 0.18 $\mu$m or less. Therefore, it has become difficult for inspection apparatuses using conventional microscopes to measure accurately line widths of the patterns of the semiconductor integrated circuits.

In particular, it is desired that inspection of a pattern of a semiconductor integrated circuit should be carried out with a resist pattern formed on a semiconductor wafer. It is, however, difficult to measure accurately and properly this resist pattern having a micro structure.

BRIEF SUMMARY OF THE INVENTION

The present invention has been proposed in view of the situation as described above and has an object of providing an inspection apparatus and an inspection method capable of inspecting a more micro pattern with high accuracy.

In case where illumination light is irradiated on an inspection target having a concave and convex pattern, such as a semiconductor integrated circuit, to pick up an image thereof, the illumination light diffracted by the concave and convex pattern causes interference so that a light intensity profile corresponding to the concave and convex pattern can be obtained, if the concave and convex pattern of the inspection target is substantially as micro as the wavelength of the illumination light.

If the diffraction efficiency of the concave and convex pattern with respect the illumination light exceeds a predetermined value, a peak corresponding to a boundary portion between a concave portion and a convex portion of the concave and convex pattern appears on the light intensity profile corresponding to this concave and convex pattern. The peak thus appearing on the light intensity profile can particularly be found clearly when reflection light or transmission light of the illumination light from the inspection target is observed in an off-focus state.

Therefore, for example, the reflection light or transmission light of the illumination light from the inspection target is observed in an off-focus state, and a distance between peaks corresponding to boundary portions concave and convex portions from the obtained intensity profile. The width of a concave or convex portion of the concave and convex pattern as the inspection target can be measured accurately on the basis of the distance between peaks.

If the state of a concave and convex pattern is inspected on the basis of a light intensity profile obtained by the diffraction interference of illumination light, it is possible to detect a very micro change of a pattern with accuracy in nano-meter order, advantageously for an inspection apparatus.

The present invention has been proposed on the basis of knowledge as described above, and provides an inspection apparatus comprising: illumination means for illuminating an inspection pattern having a concave and convex pattern with illumination light; image pickup means for picking up an image of the inspection target illuminated by the illumination means; a detection optical system for introducing reflection light or transmission light from the inspection target illuminated with the illumination means, to the image pickup means; and image processing means for preparing a light intensity profile corresponding to the concave and convex pattern of the inspection target, based on the image of the inspection target picked up by the image pickup means. Further, in this inspection apparatus, the detection optical system introduces the reflection light or transmission light in an off-focus state from the inspection target illuminated by the illumination means to the image pickup means, such that the image processing means prepares a light intensity profile having a peak corresponding to a boundary portion between a concave portion and a convex portion of the concave and convex pattern of the inspection target.

That is, in this inspection apparatus, the detection optical system introduces the reflection light or transmission light in an off-focus state, from the inspection target illuminated with the illumination light to the image pickup means, thereby to pick up an image of the inspection target in an off-focus state by the image pickup means. Further, based on the image of the inspection target picked up in this off-focus state, the image processing means prepares a light intensity profile corresponding to the concave and convex pattern of the inspection target. In this manner, a light intensity profile having a peak corresponding to a boundary portion between a concave portion and a convex portion of the inspection target is obtained.

According to this inspection apparatus, a light intensity profile having a peak corresponding to a boundary portion between a concave portion and a convex portion of the inspection target is prepared by the image processing means. Therefore, a very micro change of a pattern can be detected accurately, for example, if the state of the concave and convex pattern, such as a width of a concave or convex portion of the concave and convex pattern, is inspected on the basis of the light intensity profile obtained as described above.

Also, an inspection method according to the present invention comprises steps of: illuminating an inspection pattern having a concave and convex pattern with illumination light; introducing reflection light or transmission light from the inspection target illuminated with the illumination light, to image pickup means, and picking up an image of the inspection target by image pickup means; preparing a light intensity profile having a peak corresponding to a boundary between a concave portion and a convex portion of the concave and convex pattern of the inspection target, based on the image of the inspection target picked up by the image pickup means; and inspecting a state of the concave and convex pattern of the inspection target, based on the intensity profile obtained.

According to this inspection method, it is possible to detect properly a very micro change of a pattern with accuracy of nano-meter order.

According to the present invention, an image of an inspection target having a concave and convex pattern is picked up in an off-focus state by an image pickup element. Based on this image, the image processing means prepares a light intensity profile having a peak corresponding to a boundary portion between a concave portion and a convex portion of the concave and convex pattern of the inspection target. If the width of the concave or convex portion of the concave and convex pattern or the state of the concave and convex pattern is inspected on the basis of the light intensity profiled thus obtained, it is possible to detect accurately a very micro change of a pattern.

Also, in the inspection method according to the present invention, a light intensity profile having a peak corresponding to a boundary portion between a concave portion and a convex portion of the concave and convex pattern of the inspection target is prepared on the basis of the image of the inspection target picked up in an off-focus state. Based on the prepared intensity profile, the state of the concave and convex pattern of the inspection target is inspected, so that a very micro change of a pattern can be detected accurately.

DETAILED DESCRIPTION OF THE INVENTION

In the following, embodiments of the present invention will be explained with reference to the drawings.

Figure 1:
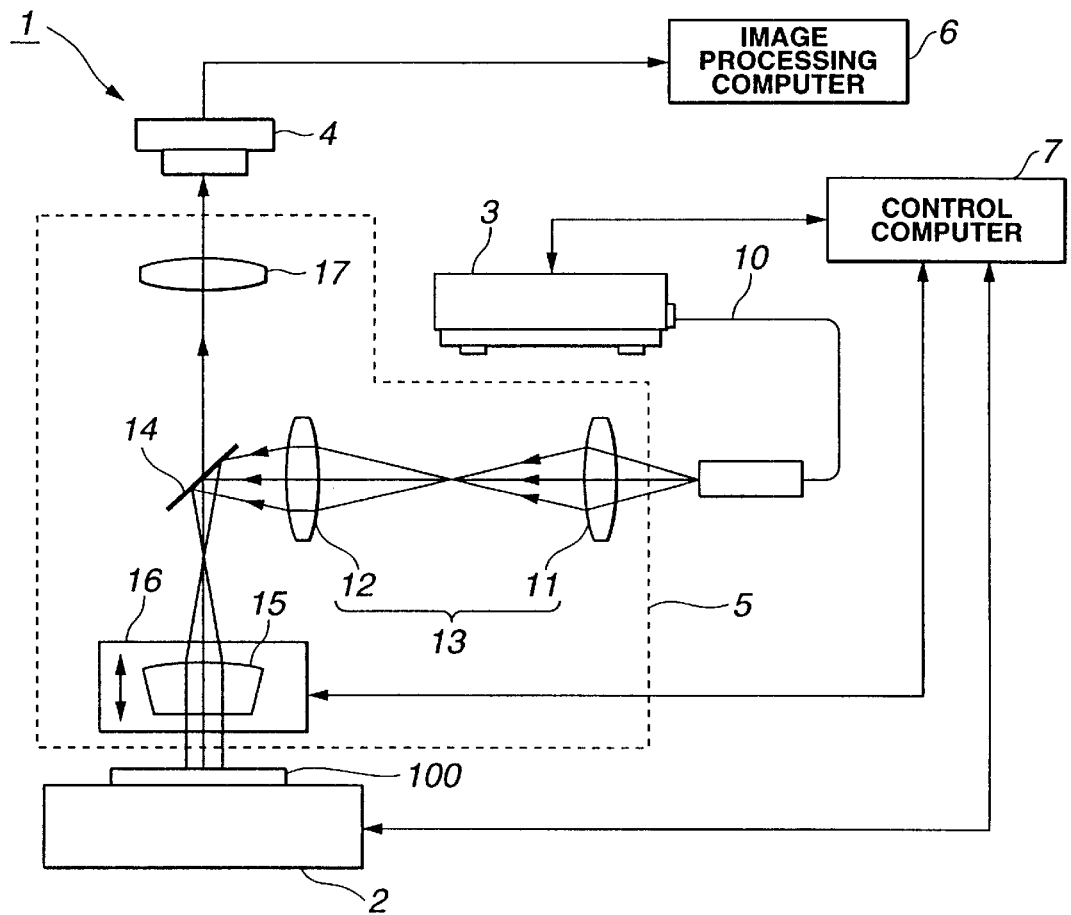
FIG. 1 is a view showing a structural example of an inspection apparatus to which the present invention is applied.

FIG. 1 shows a structural example of an inspection apparatus to which the present invention is applied. The inspection apparatus 1 shown in FIG. 1 is constructed to be capable of measuring a line width of a wiring pattern of a semiconductor integrated circuit formed on a semiconductor wafer.

As shown in FIG. 1, the inspection apparatus comprises a movable stage 2 which supports a semiconductor wafer 100 to be movable, a light source 3 which emits illumination light to illuminate the semiconductor wafer 100 set on the movable stage 2, an image pickup element 4 for picking up an image of the semiconductor wafer 100 illuminated with the illumination light, an optical system 5 or guiding the illumination light emitted from the light source to the semiconductor wafer 100 set on the movable stage 2 and for guiding reflection light from the semiconductor wafer 100 illuminated with the illumination light, an image processing computer 6 which processes the image picked up by the image pickup element 4, and a control computer 7 which controls operation of the entire inspection apparatus 1.

The movable stage 2 comprises, for example, X- and Y-stages for moving the semiconductor wafer 100 set on the movable stage 2 in the horizontal direction, a Z-stage for moving the semiconductor wafer 100 in the vertical direction, a e-stage for rotating the semiconductor wafer 100, and a suction plate for suctioning the semiconductor wafer 100 to fix it to the movable stage 2. Further, the movable stage 2 operates the other stages described above under control from the control computer 7, thereby to move the portion to be inspected of the semiconductor wafer 100 to a predetermined inspection position.

An ultraviolet solid laser is used as the light source 3. The ultraviolet solid laser performs wavelength-conversion on a solid laser such as a YAG laser or the like with use of non-linear optical crystal, thereby to emit a deep ultraviolet (DUV) laser beam having a wavelength of about 266 nm, for example.

The inspection ability of the inspection apparatus depends on the wavelength of the illumination light to be irradiated on an inspection target. Illumination light with a shorter wavelength of the illumination light enables inspection of a more micro pattern. The inspection apparatus 1 uses an ultraviolet solid laser as the light source 3 of the illumination light, so that the semiconductor wafer 100 can be illuminated with a deep ultraviolet laser beam having a short wavelength. It is therefore possible to inspect a micro pattern. In addition, the ultraviolet solid laser itself has a small size and requires no water-cooling. Thus, the ultraviolet solid laser provides easy handling, and is most suitable as the light source 3 of illumination light in the inspection apparatus 1.

As the image pickup element 4, for example, an ultraviolet CCD (charge-coupled device) camera constructed so as to obtain a high sensitivity with respect to an ultraviolet laser beam is used. The pixel size of this ultraviolet CCD camera corresponds to an optical image of 12 nm. The image pickup element 4 comprising this ultraviolet CCD camera is connected to an image processing computer 6. Further, in this inspection apparatus 1, an image of the semiconductor wafer 100 picked up by he image pickup element 4 is taken in by the image processing computer 6.

In the inspection apparatus 1, illumination light (deep ultraviolet laser beam) is emitted from the light source 3 under control from the control computer 7 and is introduced into the optical system 5 through an optical fiber 10.

The optical system 5 comprises an illumination optical system 13 constructed by two lenses 11 and 12, and the illumination light introduced to the optical system 5 through the optical fiber 10 firstly enters into the illumination optical system 13. Further, the illumination light which has passed through the illumination optical system 13 enters into a beam splitter 14, and illumination light reflected by the beam splitter 14 is irradiated on the semiconductor wafer 100 set on the movable stage 2. In this manner, the semiconductor wafer 100 set on the movable stage 2 is illuminated with illumination light as a deep ultraviolet laser beam.

Also, in this inspection apparatus 1, reflection light from the semiconductor wafer 100 illuminated with the illumination light is transmitted through the ultraviolet objective lens 15 and enters into the beam splitter 14. For example, a lens having a high numerical aperture NA of about 0.9 is used as the ultraviolet objective lens 15. In this inspection apparatus 1, a deep ultraviolet laser beam having a short wavelength is used as the illumination light, and a lens having a high numerical aperture is used as the ultraviolet objective lens 15, so that a more micro pattern can be inspected.

In addition, the ultraviolet objective lens 15 held by an objective lens movement mechanism 16 is provided on the light path of the illumination light. The objective lens movement mechanism 16 serves to hold the ultraviolet objective lens 15 to be movable in the direction along the optical axis of the lens 15, such that the distance between the ultraviolet objective lens 15 and the semiconductor wafer 100 is slightly shifted off (in an off-focus state) from the focus distance of the ultraviolet objective lens 15.

Also, in the inspection apparatus 1, the reflection light from the semiconductor wafer 100 which has been transmitted through the beam splitter 14 enters into the image pickup element 4 through an imaging lens 17. In this manner, an image of the semiconductor wafer 100 illuminated with the illumination light is magnified by the ultraviolet objective lens 15 and is picked up by the image pickup element 4.

With use of the inspection apparatus 1 structured as described above, explanation will now be made of a method for measuring a pattern width of a gate wire of a semiconductor integrated circuit formed on the semiconductor wafer 100, and that is an example of that the measurement of the pattern width of the gate wire be carried out in the stage when a resist pattern corresponding to a gate wire on the semiconductor wafer 100 has been formed.

Figure 2:
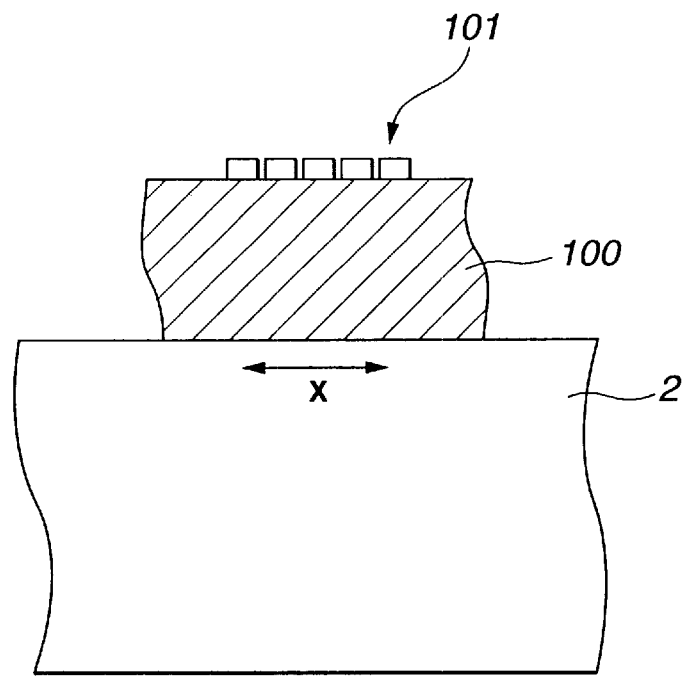
FIG. 2 is an enlarged view showing a state where a semiconductor wafer on which a resist pattern is formed is set on a movable table.

At first, as shown in FIG. 2, the semiconductor wafer 100 on which a resist pattern 101 corresponding to a gate wire is formed is set on the movable table 2. Further, the movable table 2 is driven under control of the control computer 7, and motion of the semiconductor wafer 100 is controlled, so that the portion to be inspected of the resist pattern 101 is positioned at a predetermined inspection position.

Next, the light source 3 is driven under control from the control computer 7, so as to emit a deep ultraviolet laser beam which forms illumination light. The illumination light emitted from the light source 3 is introduced to the optical system 5 through an optical fiber 101. The illumination light introduced to the optical system enters at first into the beam splitter 14 through the illumination optical system 13. Further, the illumination light reflected by the beam splitter 14 is irradiated through the ultraviolet objective lens 15 onto the semiconductor wafer 100 set on the movable table 2.

Figure 3:
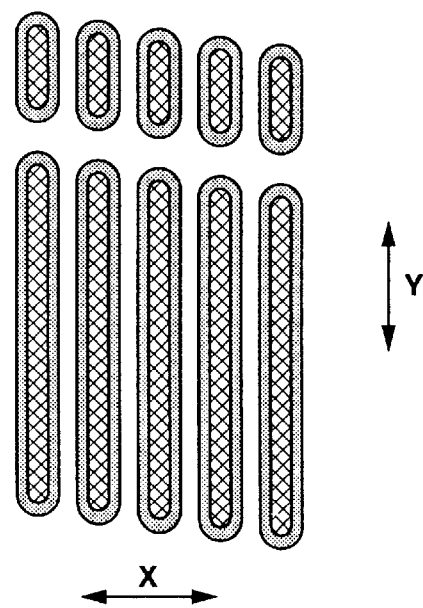
FIG. 3 is a view showing an image of a resist pattern picked up by an image pickup element.

The reflection light from the semiconductor wafer 100 illuminated with the illumination light is transmitted through the ultraviolet objective lens 15 and enters into the beam splitter 14. Further, the reflection light from the semiconductor wafer 100, which has been transmitted through the beam.splitter 14, enters into the image pickup element 4 through the imaging lens 17. In this manner, an image of the resist pattern 101 of the semiconductor wafer 100, which has been enlarged by the ultraviolet objective lens 15 as shown in FIG. 3, is picked up by the image pickup element 4.

The ultraviolet objective lens 15 is held in an off-focus state by the objective lens movement mechanism 16 which is driven under control from the control computer 7. Therefore, the image pickup element 4 picks up an image of the resist pattern 101 in an off-focus state.

The image of the resist pattern 101 picked up in an off-focus state by the image pickup element 4 is taken in by the image processing computer 6. Further, the image processing computer 6 processes the image of the take-in resist pattern 101 thereby to prepare an intensity profile of light, as shown in FIG. 4.

Figure 4:
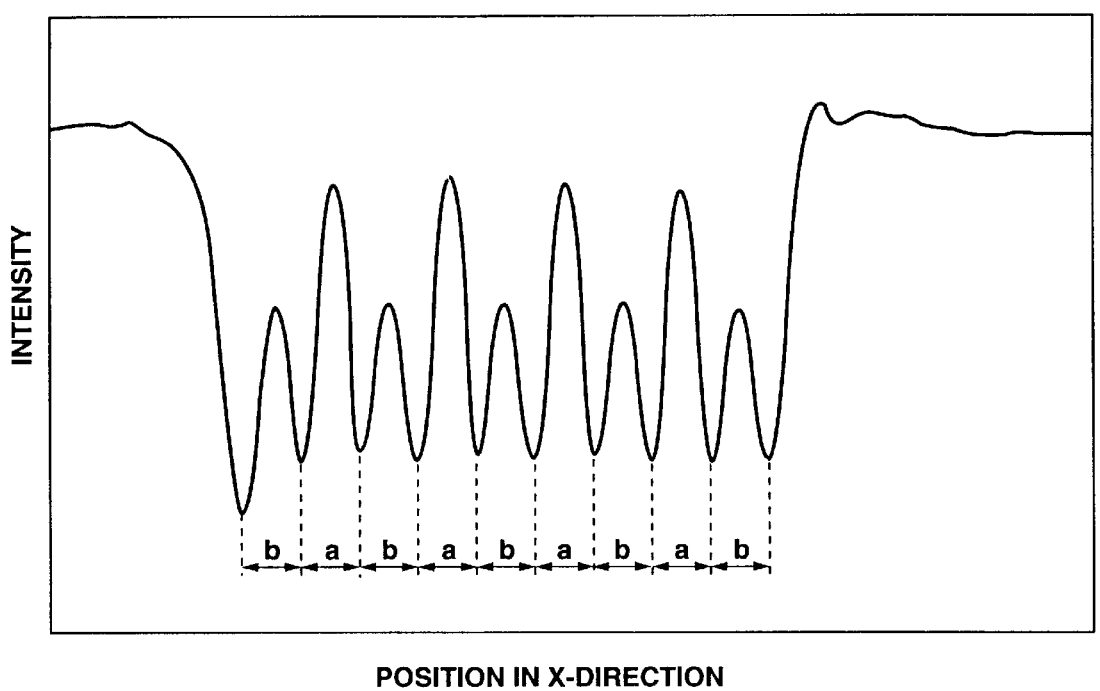
FIG. 4 is a graph showing an example of an intensity profile prepared by an image processing computer.

The intensity profile shown in FIG. 4 is obtained when illumination light diffracted by the resist pattern 101 constructed by concaves and convexes causes interference near gaps therebetween. This profile corresponds to the concaves and convexes of the resist pattern 101. That is, the large crests appearing on the intensity profile (e.g., the portions indicated at the reference a in FIG. 4) correspond to concave portions of the resist pattern 101, and portions each appearing between two large crests (e.g., the portions indicated at the reference b in FIG. 4) on the intensity profile correspond to convex portions of the resist pattern 101. Also on the intensity profile, a small crest appears between every two large crests, and a peak as a trough appears between every adjacent small and large crests. The peaks as troughs correspond to boundary portions between concave and convex portions (hereinafter called pattern edges).

In the inspection apparatus 1 to which the present invention is applied, it is thus possible to obtain an intensity profile on which peaks as troughs appear in correspondence with pattern edges of the resist pattern 101. It is therefore possible to measure the width of each convex portion (hereinafter called a line width) of the resist pattern 101 from the intensity profile. That is, on the intensity profile obtained by the inspection apparatus 1, the portion sandwiched between two peaks as troughs corresponds to the width of a convex portion. Accordingly, a line width of the resist pattern 101 can be measured by obtaining the distance between two peaks as troughs.

Explained now will be a method for measuring a line width of the resist pattern 101 from an intensity profile prepared by the image processing computer 6.

Figure 5:
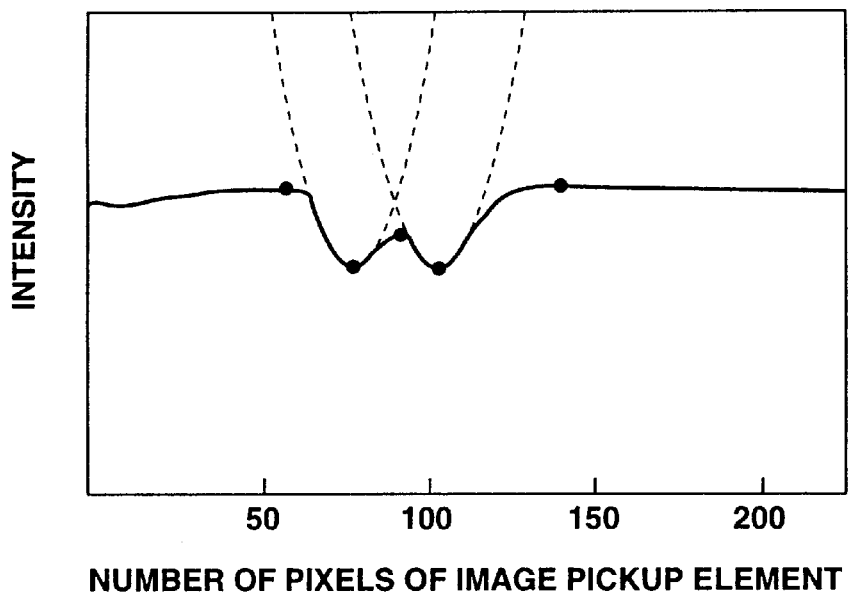
FIG. 5 is a graph showing an intensity profile obtained when an image of a resist pattern having a resist thickness of 400 nm and a line width of 173 nm is picked up in an off-focus state and this image is taken in by the image processing computer.

For example, a resist pattern 101 which has a resist thickness of 400 nm and a line width of 173 nm is picked in an off-focus state by the image pickup element 4, and this image is taken in by the image processing computer 6. Then, an intensity profile as shown in FIG. 5 is prepared by the image processing computer 6.

To measure a line width of the resist pattern 101 from an intensity profile prepared by the image processing computer 6, at first, the part of a trough of the intensity profile is fitted to a quadric function. Further, an extreme of the quadric function is detected as a peak of a trough portion. In this manner, it is possible to obtain the positions of peaks of trough portions, which correspond to pattern edges of the resist pattern 101, with a high accuracy equivalent to the pixel size of the image pickup element 4 or less.

Next a distance between adjacent peaks of two troughs is measured. The distance between peaks of two troughs corresponds a line width of the resist pattern 101. An obtained distance between peaks of two troughs (i.e., an observation value of a line width of the resist pattern 101) is greater than an actual value (absolute value) of the line width of the resist pattern 101. For example, in this case, an observation value measured from the intensity profile is 305 nm although the absolute value of the line width of the resist pattern 101 is 173 nm.

Thus, the observation value measured from the intensity profile is greater than the absolute value of the line width of the resist pattern 101 because the image of the resist pattern 101 is picked up in an off-focus state and the intensity profile is prepared on the basis of the image picked up in this off-focus state.

Figure 6:
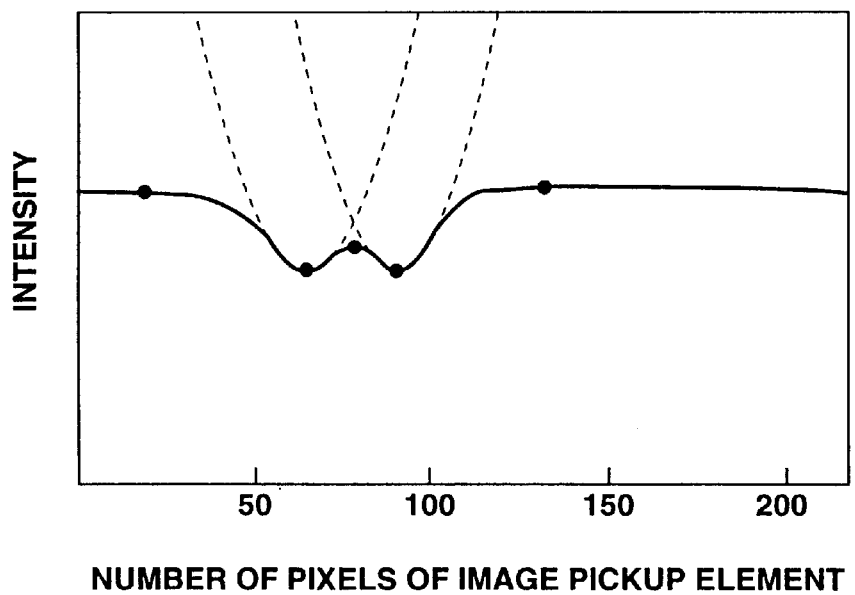
FIG. 6 is a graph showing an intensity profile obtained when an image of a resist pattern having a resist thickness of 400 nm and a line width of 355 nm is picked up in a correctly focused state and this image is taken in by the image processing computer.

To make comparison, an image of a resist pattern which had a resist thickness of 400 nm and a line width of 355 nm was picked up by the image pickup element 4 correctly focused. This image was taken in by the image processing computer 6 to prepare an intensity profile. As shown in FIG. 6, it was possible to obtain an intensity profile which is substantially the same as that obtained in case where the resist pattern 101 having a line width of 173 nm was observed in an off-focus state. Further, a distance between peaks of two adjacent troughs appearing on the intensity profile of the comparative example was measured to find an observation value of 302 nm.

If an intensity profile is thus prepared on the basis of the image of the resist pattern 101 picked up in a correctly focused state and an observation value of a line width of the resist pattern 101 is obtained, the observation value becomes equal to or less than the absolute value of the line width of the resist pattern 101.

Figure 7:
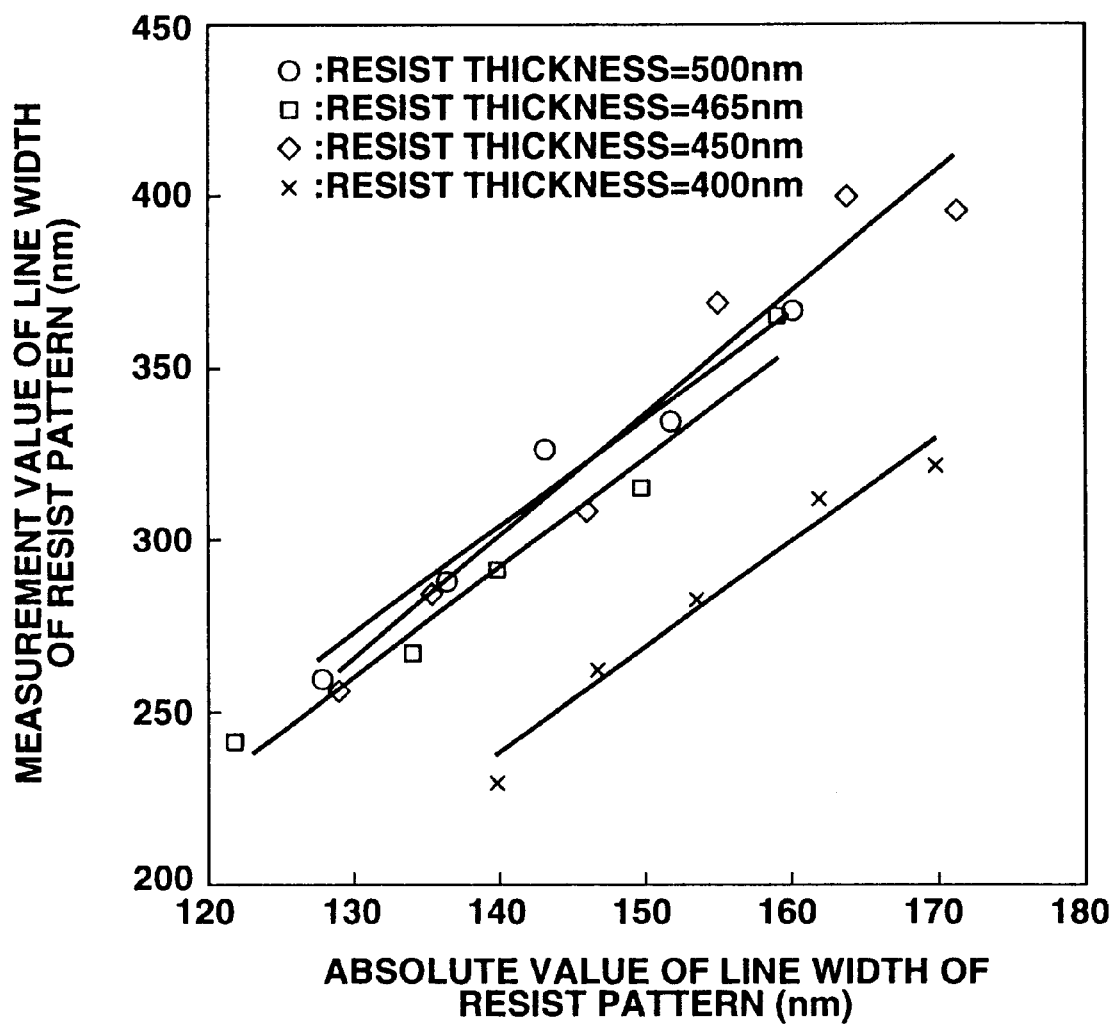
FIG. 7 is a view showing a relationship between a measurement value of a line width of a resist pattern and an absolute value thereof.
Figure 8:
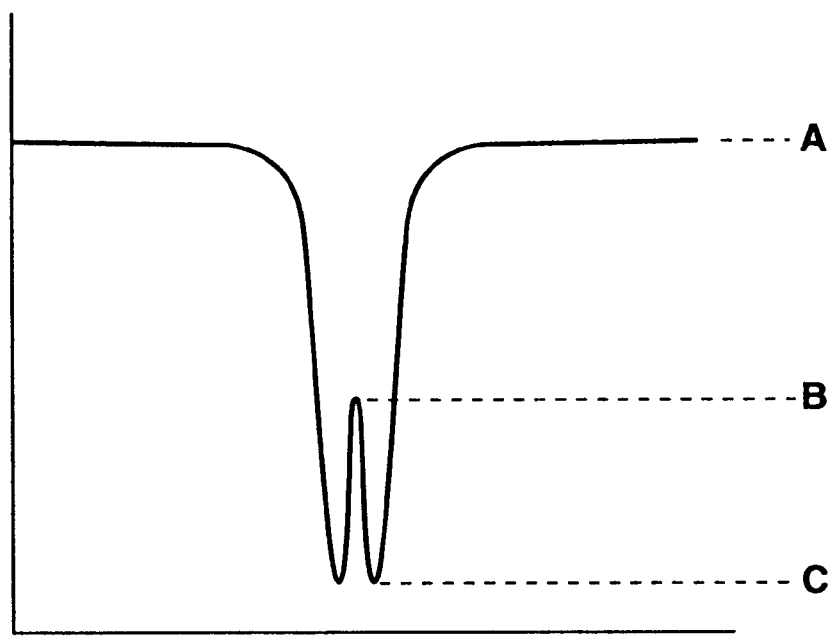
FIG. 8 is a view for explaining definition of contrast of a peak which forms a trough on an intensity profile.

At this time, investigation was made on a relationship between the observation value of the line width of the resist pattern 101 obtained by observation in an off-focus state and the absolute value of the line width of the resist pattern 101, to find a substantially linear relationship therebetween as shown in FIG. 7. In FIG. 7, the longitudinal axis represents the measurement value of a line width obtained when observing the resist pattern 101 in an off-focus state, and the lateral axis represents the absolute value of the line width of the resist pattern 101. The absolute value of the line width of the resist pattern 101 is a value measured by using a scanning electron microscope (SEM). In FIG. 7, each circle mark denotes a measurement value of a resist pattern 101 having a resist thickness of 500 nm, and each square mark denotes a measurement result of a resist pattern 101 having a resist thickness of 465 nm. Also, in FIG. 7, each diamond mark denotes a measurement value of a resist pattern 101 having a resist thickness of 450 nm, and each cross mark denotes a measurement result of a resist pattern 101 having a resist thickness of 400 nm.

As shown in FIG. 7, there is a substantially linear relationship between the observation value of the line width obtained when observing a resist pattern 101 in an off-focus state and the absolute value of the line width of the resist pattern 101. The inclination of the line is substantially constant even when the resist thickness is changed.

Therefore, the absolute value of a line width of a resist pattern 101 can be obtained by correcting an observation value of the line width of the resist pattern 101 measured from an intensity profile if the ratio of the observation value of the line width of the resist pattern 101 to the absolute value thereof is previously known.

As described above, a line width of a resist pattern 101 can be measured accurately if an intensity profile is prepared on the basis of an image of the resist pattern picked up in an off-focus state and the line width of the resist pattern 101 is obtained from the intensity profile. When the line width of the resist pattern 101 changes, the change of the line width can be detected very accurately.

That is, the measurement value of the line width of the resist pattern 101 obtained on the basis of an intensity profile prepared by the inspection apparatus 1 is a greater value than the absolute value of the line width of the resist pattern 101, and there is a substantially linear relationship therebetween. Therefore, when the line width of the resist pattern 101 changes, the measurement value of the line width of the resist pattern 101 obtained on the basis of an intensity profile changes by a greater change amount than an actual change amount of the line width. For example, in the case shown in FIG. 7, the inclination of the line representing the relationship between the observation value and the absolute value of a line width of the resist pattern 101 is about 2.5. Accordingly, when the line width of the resist pattern 101 changes by 10 nm, for example, the measurement value of the line width of the resist pattern 101 changes by about 25 nm. Therefore, even a very slight change of a line width can be properly detected, if the change of the line width of a resist pattern 101 is detected from measurement values of the line width of the resist pattern which are obtained on the basis of an intensity profile prepared by the inspection apparatus 1.

Also, in this inspection apparatus 1, an obtained measurement value of a line width of a resist pattern 101 is greater than the absolute value of the line width of the resist pattern 101. It is therefore possible to set a relatively small imaging magnification in the image pickup element 4, so that limitations to the ultraviolet objective lens 15 and other optical systems can be relaxed relatively.

Meanwhile, in the inspection apparatus 1 to which the present invention is applied, the intensity profile prepared by the image processing computer 6 varies depending on the off-focus amount when picking up an image of the resist pattern 101 by the image pickup element 4. Further, an intensity profile which maximizes the contrast of a peak as a trough corresponding to a pattern edge of the resist pattern 101 can be obtained if the off-focus amount is set to an optimal value in correspondence with the shape of the resist pattern 101 and the structure of the optical system. If the line width of the resist pattern 101 is measured on the basis of the intensity profile thus obtained, it is possible to inspect accurately a very fine resist pattern 101 having a line width of 0.18 $\mu$m or less.

The contrast of a peak as a trough is a value obtained by (B−C)/(A−C) where the intensity of a large crest is A, the intensity of a small crest is B, and the intensity of a peak as a trough is C. The definition of the contrast of a peak as a trough is not limited thereto. For example, the contrast of a peak as a trough may be defined as a value obtained by (B−C)/(B+C) where the intensity of a large crest is A, the intensity of a small crest is B, and the intensity of a peak as a trough is C.

In the inspection apparatus 1 to which the present invention is applied, the objective lens movement mechanism 16 is driven under control from the control computer 7, to move the ultraviolet objective lens 15 in its optical axis, so that the off-focus amount is set to an optimal value which maximizes the contrast of a peak as a trough on an intensity profile. For example, in case where a resist pattern 101 formed by an isolated pattern having a resist thickness of 400 nm, a line width of 173 nm, and a rectangular cross-sectional shape is observed in the inspection apparatus 1 which has an optical system as described above, an intensity profile which maximizes the contrast of a peak as a trough is obtained when the off-focus amount is 0.5 to 0.6 µm. Therefore, in case of observing the resist pattern 101 as described above in the inspection apparatus 1, the ultraviolet objective lens 15 is moved to set an off-focus state in which the distance between the ultraviolet objective lens 15 and the semiconductor wafer 100 set on the movable stage 2 is shifted by 0.5 to 0.6 µm from the focus distance of the ultraviolet objective lens 15.

Setting of the off-focus amount is not limited to the example in which the ultraviolet objective lens 15 is moved as described above. For example, the Z-stage of the movable stage 15 may be driven under control from the control computer 7 to move and operate the semiconductor wafer 100 in the vertical direction, to achieve the setting.

As has been explained above, in case of measuring a line width of a resist pattern 101 in the inspection apparatus 1 to which the present invention is applied, for example, an image of the resist pattern 101 is picked up in an off-focus state by the image pickup element 4, and this image is taken in by the image processing computer 6, to prepare an intensity profile corresponding to the resist pattern 101. Based on this intensity profile, the line width of the resist pattern 101 is measured. Therefore, the line width of a micro resist pattern 101 can be measured with high accuracy.

In particular, patterns of semiconductor integrated circuits have become more and more micro in recent years, and their line widths have become 0.18 µm or less. In the inspection apparatus 1 according to the present invention, an intensity profile having peaks corresponding to pattern edges can be obtained by setting the off-focus amount to an optimal value when picking up an image of a resist pattern 101, even if a very micro resist pattern 101 having a line width of 0.18 µm or less is inspected. Based on the intensity profile, it is possible to inspect accurately the very micro resist pattern 101 having a line width of 0.18 µm or less. Accordingly, the inspection apparatus 1 is very advantageous for inspection of patterns of semiconductor integrated circuits which have become so micro.

Also, the inspection apparatus 1 inspects a resist pattern 101 by optically picking up an image of the resist pattern 101. Therefore, the inspection apparatus 1 does not requires vacuum, unlike a scanning electron microscope or an atomic force microscope. Thus, according to the inspection apparatus 1, the resist pattern 101 can be inspected easily and rapidly.

An observation value of a line width of a resist pattern 101, which is obtained from an intensity profile prepared by the inspection apparatus 1, is different from the absolute value of the line width of the resist pattern 101. Therefore, the ratio of the observation value to the absolute value must be obtained in advance, in order to correct the observation value of the line width of the resist pattern 101 thereby to obtain an absolute value thereof. Since there is a substantially linear relationship between the observation value and the absolute value of the resist pattern 101, the ratio of the line width of the resist pattern 101 to the absolute value thereof is constant unless the shape or inspection condition of the resist pattern 101 is changed. Accordingly, an absolute value of a line width of a resist pattern 101 can be obtained simply and rapidly by correcting an observation value of a line width of a resist pattern 101, which is obtained by the inspection apparatus 1, if the ratio of the observation value of the resist pattern 101 to the absolute value thereof is previously obtained by measuring the absolute value of the resist pattern 101 with use of a scanning electron microscope or the like, only when the shape of the resist pattern 101 to be inspected is changed or when the inspection condition is changed.

The above explanation has been made with reference to an example of a case where a line width of a resist pattern 101 formed on a semiconductor wafer 100 is measured. However, in the inspection apparatus 1 to which the present invention is applied, any kind of inspection target that has a concave and convex pattern can be inspected accurately.

What is claimed is:

1. An inspection apparatus, comprising:
   an illumination means for illuminating an inspection pattern having a concave and convex pattern; the concave pattern having a concave portion and the convex pattern having a convex portion;
   an image pickup means for picking up an image of the inspection pattern illuminated by the illumination means;
   a detection optical system for introducing light from the inspection pattern illuminated by the illumination means to the image pickup means; and
   an image processing means for preparing a light intensity profile corresponding to the concave and convex pattern of the inspection pattern, the light intensity profile being based on the image of the inspection pattern picked up by the image pickup means, wherein
   the detection optical system introduced the light in an off-focus state from the inspection pattern illuminated by the illumination means to the image pickup means, such that the image processing means prepares the light intensity profile having a peak, the peak corresponding to a boundary portion between the concave portion and the convex portion wherein at least one of the concave portion and the convex portion has a width up to and including 0.18 µm.

2. The inspection apparatus according to claim 1, wherein the off-focus amount of the detection optical system is set such that the image processing means prepares the light intensity profile in which contrast at the peak corresponding to the boundary portion between the concave portion and convex portion of the concave and convex pattern of the inspection pattern maximized.

3. The inspection apparatus according to claim 1, wherein the peak corresponding to the boundary portion between the concave portion and the convex portion of the intensity profile prepared is fitted to a function by the image processing means, and an observation value of the width of the concave portion or the convex portion is detected with reference to an extreme of the function.

4. The inspection apparatus according to claim 3, wherein the observation value of the width of the concave portion or the convex portion, detected by the image processing means, is greater than an absolute value of the width of the concave portion or the convex portion, and
   the absolute value of the width of the concave portion or the convex portion is obtained by correcting the observation value of the width of the concave portion or the convex portion, detected by the image processing means.

5. The inspection apparatus according to claim 4 wherein a ratio of a change of the observation value of the width of the concave portion or the convex portion, detected by the image processing means, is greater than a ratio of a change of the absolute value of the width of the concave portion or the convex portion.

6. The inspection apparatus according to claim 1, wherein the illumination means illuminates the inspection pattern using ultraviolet light as the illumination light.

7. An inspection method, comprising:

illuminating an inspection pattern having a concave and convex pattern with illumination light, the concave pattern having a concave portion and the convex pattern having a convex portion;

introducing light in an off-focus state from the inspection pattern illuminated with the illumination light, to an image pickup means, and picking up an image of the inspection pattern by the image pickup means;

preparing a light intensity profile having a peak corresponding to a boundary portion between the concave portion the convex portion wherein at least one of the concave portion or the convex portion has a width up to and including, the light intensity profile being based on the image of the inspection pattern picked up by the image pickup means; and inspecting a state of the concave and convex pattern of the inspection pattern, based on the intensity profile obtained.

8. The inspection method according to claim 7, wherein the off-focus amount of the light to be introduced to the image pickup means from the inspection target is set so as to obtain the light intensity profile in which contrast at the peak corresponding to the boundary portion between the concave portion and convex portion is maximized.

9. The inspection method according to claim 7, wherein the peak corresponding to the boundary portion between the concave portion and the convex portion of the intensity profile prepared is fitted to a function, and an observation value of the width of the concave portion or the convex portion is detected with reference to an extreme of the function.

10. The inspection method according to claim 9, wherein the observation value of the width of the concave portion or the convex portion is greater than an absolute value of the width of the concave portion or the convex portion, and the absolute value of the width of the concave portion or the convex portion is obtained by correcting the observation value of the width of the concave portion or the convex portion.

11. The inspection method according to claim 10, wherein to obtain the absolute value by correcting the observation value, the absolute value of the concave and convex pattern is measured in advance with use of a scanning electron microscope or the like, to obtain a ratio of the observation value of the concave and convex pattern to the absolute value of the concave and convex pattern, and the observation value obtained by inspection based on the ratio is corrected to obtain the absolute value.

12. The inspection method according to claim 10 wherein a ratio of a change of the observation value of the width of the concave portion or the convex portion is greater than a ratio of a change of the absolute value of the width of the concave portion or the convex portion.

13. The inspection method according to claim 7, wherein the inspection pattern is illuminated, using ultraviolet light as the illumination light.

* * * * *